United States Patent
Salomao et al.

(10) Patent No.: US 12,121,602 B2
(45) Date of Patent: Oct. 22, 2024

(54) ANHYDROUS SUNSCREEN COMPOSITION, PROCESS OF MANUFACTURING THE ANHYDROUS SUNSCREEN COMPOSITION AND USE OF THE ANHYDROUS SUNSCREEN COMPOSITION

(71) Applicant: L'OREAL, Paris (FR)

(72) Inventors: Bruna Rodrigues Salomao, Rio de Janeiro (BR); Lais Moreira Lima, Rio de Janeiro (BR); Wagner Pereira, Rio de Janeiro (BR); Angeles Fonolla-Moreno, Rio de Janeiro (BR)

(73) Assignee: L'OREAL, Paris (FR)

( * ) Notice: Subject to any disclaimer, the term of this patent is extended or adjusted under 35 U.S.C. 154(b) by 537 days.

(21) Appl. No.: 17/442,162

(22) PCT Filed: Mar. 29, 2019

(86) PCT No.: PCT/BR2019/050116
§ 371 (c)(1),
(2) Date: Sep. 23, 2021

(87) PCT Pub. No.: WO2020/198817
PCT Pub. Date: Oct. 8, 2020

(65) Prior Publication Data
US 2022/0168196 A1    Jun. 2, 2022

(51) Int. Cl.
| | |
|---|---|
| *A61K 8/25* | (2006.01) |
| *A61K 8/02* | (2006.01) |
| *A61K 8/29* | (2006.01) |
| *A61K 8/31* | (2006.01) |
| *A61K 8/35* | (2006.01) |
| *A61K 8/37* | (2006.01) |
| *A61K 8/49* | (2006.01) |
| *A61K 8/92* | (2006.01) |
| *A61Q 17/04* | (2006.01) |

(52) U.S. Cl.
CPC .............. *A61K 8/25* (2013.01); *A61K 8/0229* (2013.01); *A61K 8/29* (2013.01); *A61K 8/31* (2013.01); *A61K 8/35* (2013.01); *A61K 8/37* (2013.01); *A61K 8/4966* (2013.01); *A61K 8/922* (2013.01); *A61Q 17/04* (2013.01); *A61K 2800/31* (2013.01); *A61K 2800/61* (2013.01)

(58) Field of Classification Search
CPC .......... A61K 8/25; A61K 8/0229; A61K 8/29; A61K 8/31; A61K 8/35; A61K 8/37; A61K 8/922; A61K 2800/31; A61K 2800/61; A61Q 17/04
See application file for complete search history.

(56) References Cited

U.S. PATENT DOCUMENTS 9,114,076 B2    8/2015   Dumousseaux et al.

FOREIGN PATENT DOCUMENTS

| DE | 202006010652 U1 | 12/2006 | | |
|---|---|---|---|---|
| EP | 1690523 A1 | 8/2006 | | |
| EP | 3056192 | * 8/2016 | | |
| EP | 3056192 A1 | * 8/2016 | ............... | A61K 8/25 |
| EP | 2775993 | * 10/2018 | | |
| WO | WO-0247620 A2 | * 6/2002 | ............... | A61K 8/02 |
| WO | WO 2002247620 | * 6/2002 | | |
| WO | WO 2012085855 | * 6/2012 | | |
| WO | 2013068236 A1 | 5/2013 | | |
| WO | 2015186078 A1 | 12/2015 | | |
| WO | 2016058180 A1 | 4/2016 | | |

OTHER PUBLICATIONS

Yang (Materials letters 65 (2011) 1060-1062.*
International Search Report and Written Opinion issued on Nov. 20, 2019 for corresponding PCT Application No. PCT/BR2019/050116.

* cited by examiner

*Primary Examiner* — Shirley V Gembeh
(74) *Attorney, Agent, or Firm* — POLSINELLI PC

(57) ABSTRACT

ANHYDROUS SUNSCREEN COMPOSITION, PROCESS OF MANUFACTURING THE ANHYDROUS SUNSCREEN COMPOSITION AND USE OF THE ANHYDROUS SUNSCREEN COMPOSITION The present disclosure is directed to high SPF anhydrous sunscreen compositions. More specifically, the present disclosure is directed to high SPF anhydrous sunscreen compositions having enhanced anti-oiliness and anti-acne effect, as well as good hardness properties and dry touch to the skin after application combined with matt effect, comprising high concentration of silica aerogel, at least one emollient, a wax blend and an UV filter system. The present invention also discloses a process of manufacturing the anhydrous sunscreen compositions and uses of the sunscreen compositions.

19 Claims, 9 Drawing Sheets

ANHYDROUS SUNSCREEN COMPOSITION, PROCESS OF MANUFACTURING THE ANHYDROUS SUNSCREEN COMPOSITION AND USE OF THE ANHYDROUS SUNSCREEN COMPOSITION

CROSS-REFERENCE TO RELATED APPLICATIONS

This application is a national stage application (under 35 U.S.C. § 371) of PCT/BR2019/050116, filed Mar. 29, 2019, which is incorporated herein by reference in its entirety.

FIELD OF THE INVENTION

The present disclosure is directed to high SPF anhydrous sunscreen compositions. More specifically, the present disclosure is directed to high SPF anhydrous sunscreen compositions having enhanced anti-oiliness and anti-acne effect, as well as good hardness properties and dry touch to the skin after application combined with matt effect, comprising high concentration of silica aerogel, at least one emollient, a wax blend and an UV filter system. The present invention also discloses a process of manufacturing the anhydrous sunscreen compositions and uses of the sunscreen compositions.

BACKGROUND OF THE INVENTION

The photoprotection of keratinous materials, including both skin and hair, is considered of great importance in order to protect from sun-damage, sunburn, photo-aging, as well as to decrease the chances of skin cancer development caused by exposure to ultraviolet ("UV") radiation. There are typically two types of UVA/UVB sunscreen compositions used to accomplish photoprotection, namely, inorganic UV filters and organic UV filters.

The degree of UV protection afforded by a sunscreen composition is directly related to the amount and type of UV filters contained therein. The higher the amount of UV filters, the greater the degree of UV protection (UVA/UVB). Particularly, sunscreen compositions must provide good protection against the sun, a measure of which is the Sun Protection Factor (SPF) value, yet have satisfactory sensory perception, such as a smooth but not greasy feel upon application.

Usually, sunscreen products may be in the form of lotions, milks, creams, gels, gel creams, foams, sprays and sticks. Such products can be anhydrous or in the form of emulsions, generally containing sunscreen actives that are solubilized, emulsified, or dispersed in a vehicle, which is topically applied onto the skin. The sunscreen actives, typically through the aid of polymers and other ingredients included in the vehicle, form a thin, protective, and often water-resistant layer on the skin.

Hydrophobic silica is commonly known in the cosmetic industry for providing anti-oiliness and anti-acne effects, including in sunscreen compositions. However, the maximum concentration of silica in a composition is limited, due to its high hydrophobic properties, thereby rendering the composition instable when high concentrations of silica are applied. In this sense, sunscreen compositions are usually limited to have about 0.5% by weight of silica, relative to the total weight of the composition.

Thus, there has been a need for sunscreen compositions having higher concentrations of silica, in order to enhance the anti-oiliness and anti-acne effects thereof. The challenge of incorporating high concentrations of silica in the sunscreen composition is not only limited due to the hydrophobic nature of the silica, but there is also the challenge on formulating stable compositions while preserving satisfactory properties of the product, such as hardness, high SPF and dry touch to the skin after application combined with matt effect.

Considering the current drawbacks of the state of the art and the difficulties to overcome them, the inventors formulated an anhydrous sunscreen composition that enables the high concentration of silica aerogel by combining a specific blend of waxes, at least one emollient and a UV filter system. The anhydrous sunscreen composition of the present invention having high concentration of silica surprisingly showed enhanced anti-oiliness and anti-acne effects, good hardness properties, high SPF values, dry touch to the skin after application combined with matt effect and no white film formation.

SUMMARY OF THE INVENTION

The present disclosure relates to anhydrous sunscreen compositions having enhanced anti-oiliness and anti-acne effects, good hardness properties, high SPF values and dry touch to the skin after application combined with matt effect, comprising high concentration of silica aerogel, at least one emollient, a wax blend and an UV filter system. The present disclosure is also directed to a process of manufacturing the anhydrous sunscreen compositions and uses of the anhydrous sunscreen compositions.

Other features and advantages of the present invention will be apparent from the following more detailed description of the desirable embodiments which illustrates, by way of example, the principles of the invention.

DETAILED DESCRIPTION OF THE INVENTION

Figure 1:
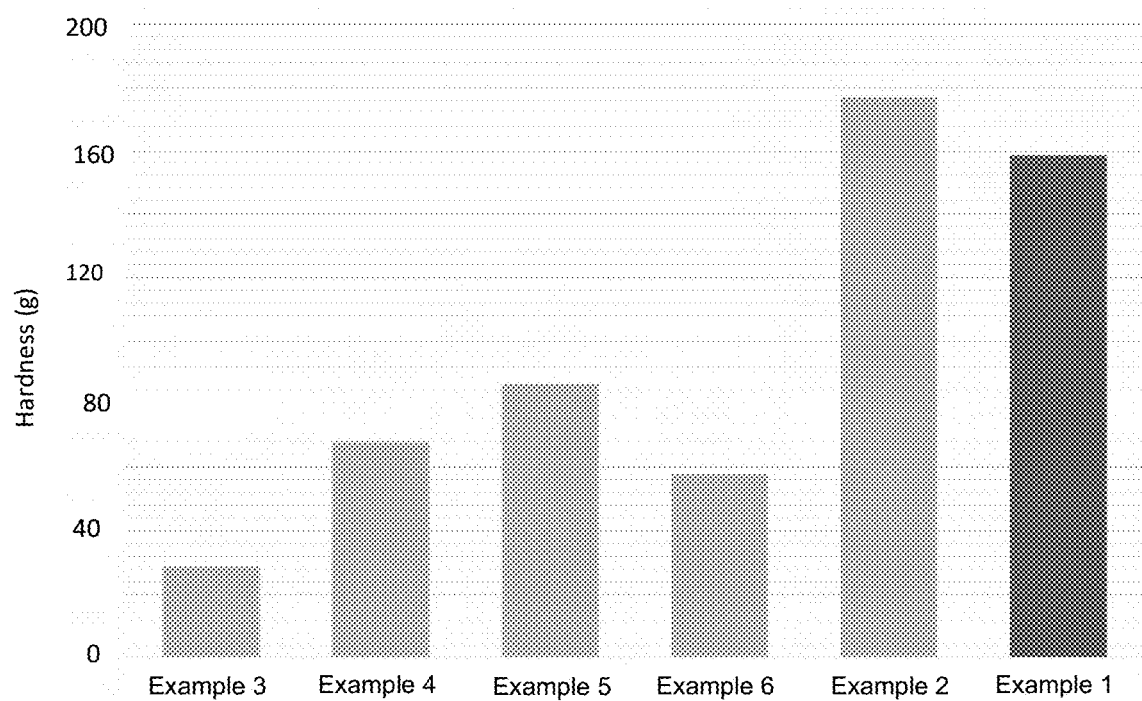
FIG. 1. shows the results of the hardness test performed on anhydrous sunscreen compositions according to Examples 1 to 6.
Figure 2:
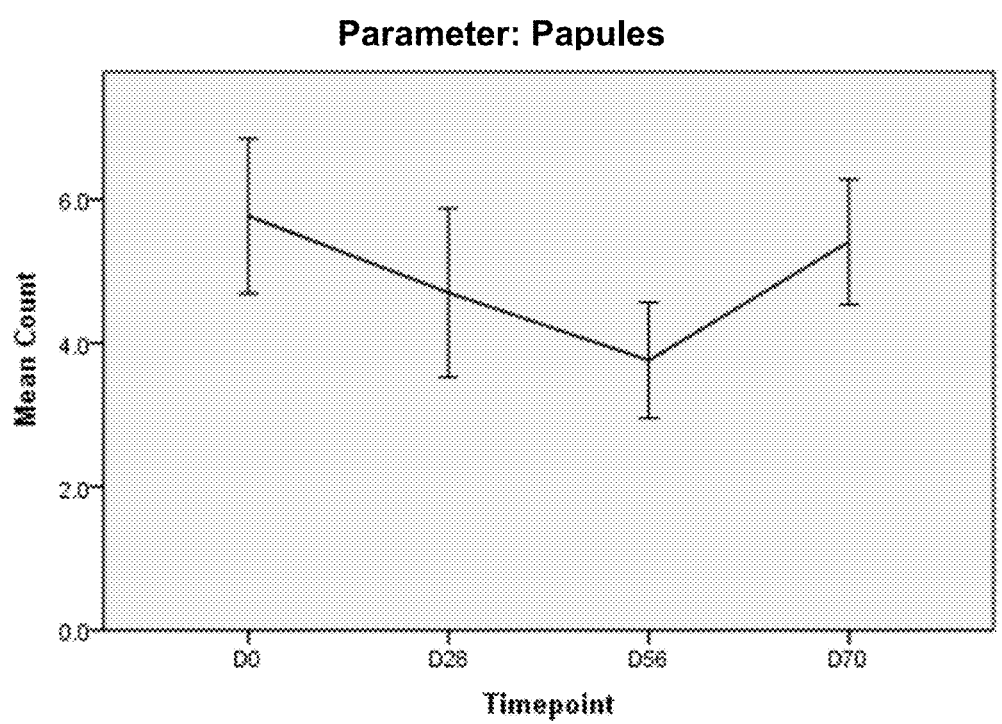
FIG. 2. Shows the evolution of the mean count of papules across time of volunteers under daily use of an anhydrous sunscreen composition according to the present invention.
Figure 3:
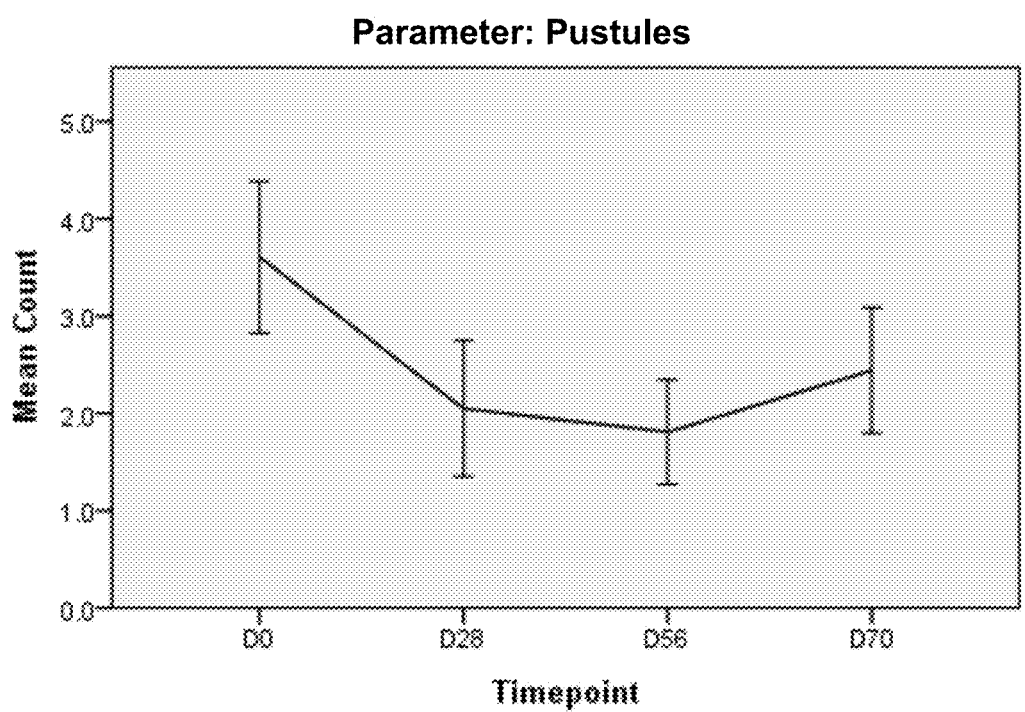
FIG. 3. Shows the evolution of the mean count of pustules across time of volunteers under daily use of an anhydrous sunscreen composition according to the present invention.
Figure 4:
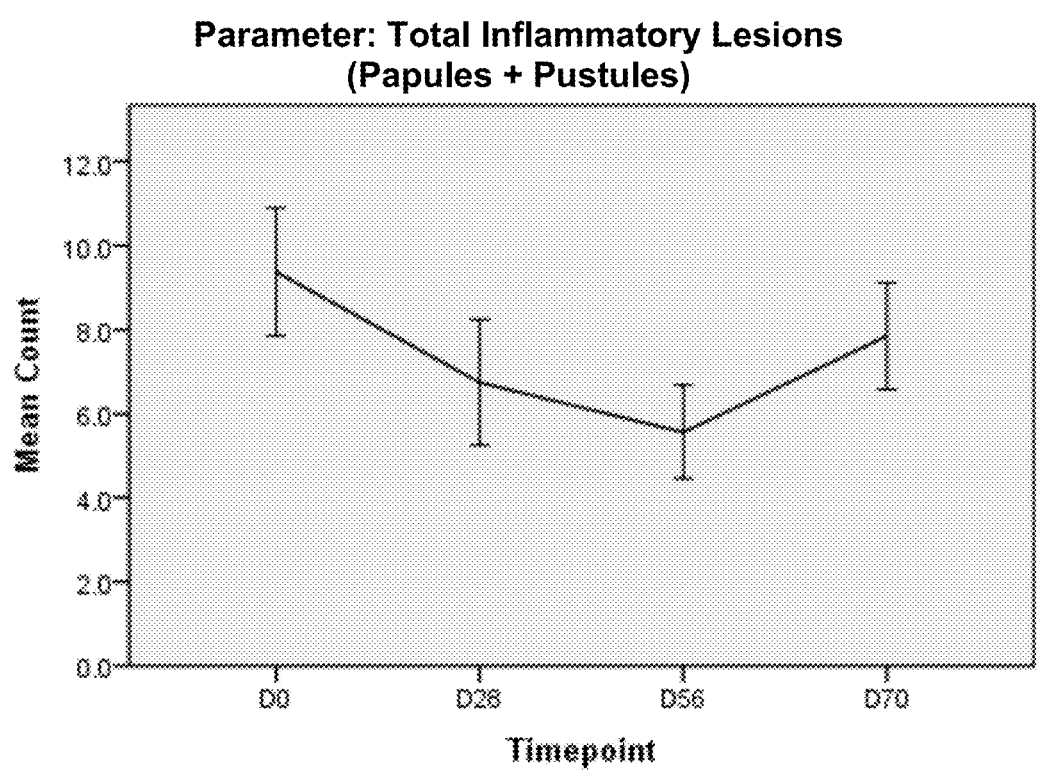
FIG. 4. Shows the evolution of the mean count of total inflammatory lesions across time of volunteers under daily use of an anhydrous sunscreen composition according to the present invention.
Figure 5:
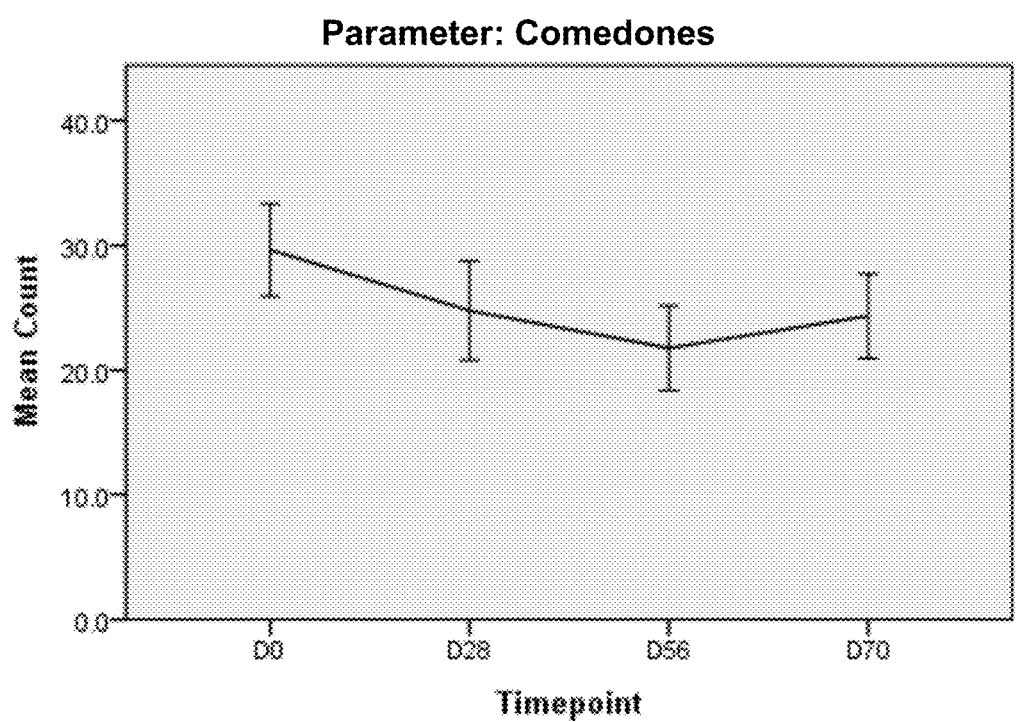
FIG. 5. Shows the evolution of the mean count of comedones across time of volunteers under daily use of an anhydrous sunscreen composition according to the present invention.
Figure 6:
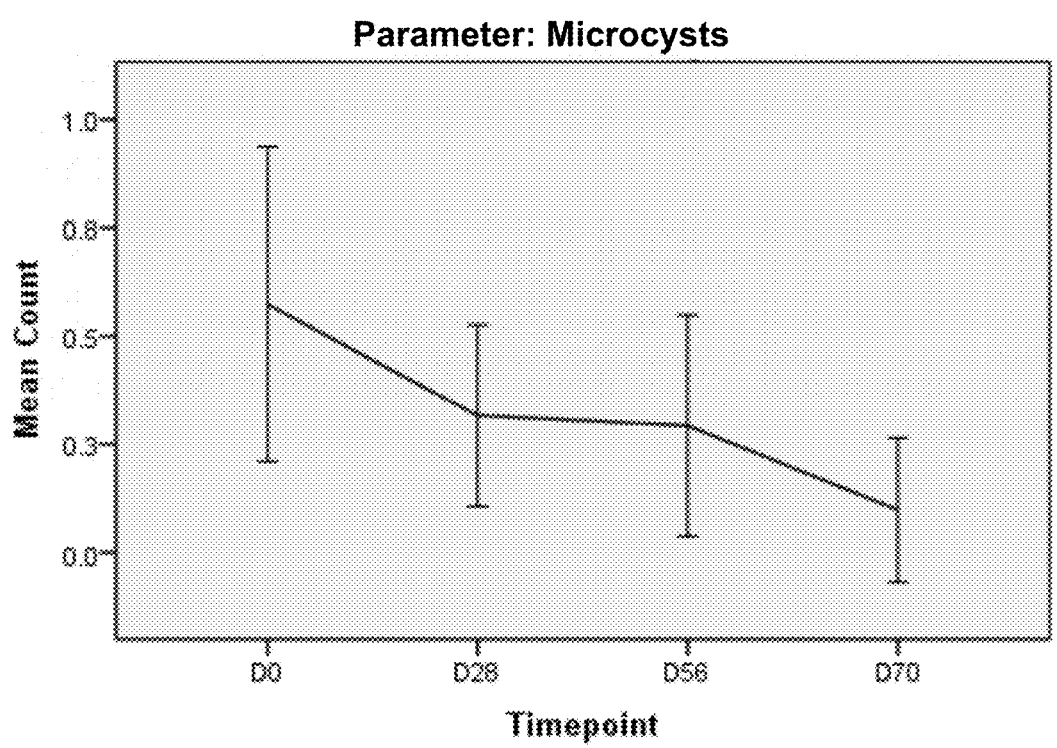
FIG. 6. Shows the evolution of the mean count of microcysts across time of volunteers under daily use of an anhydrous sunscreen composition according to the present invention.
Figure 7:
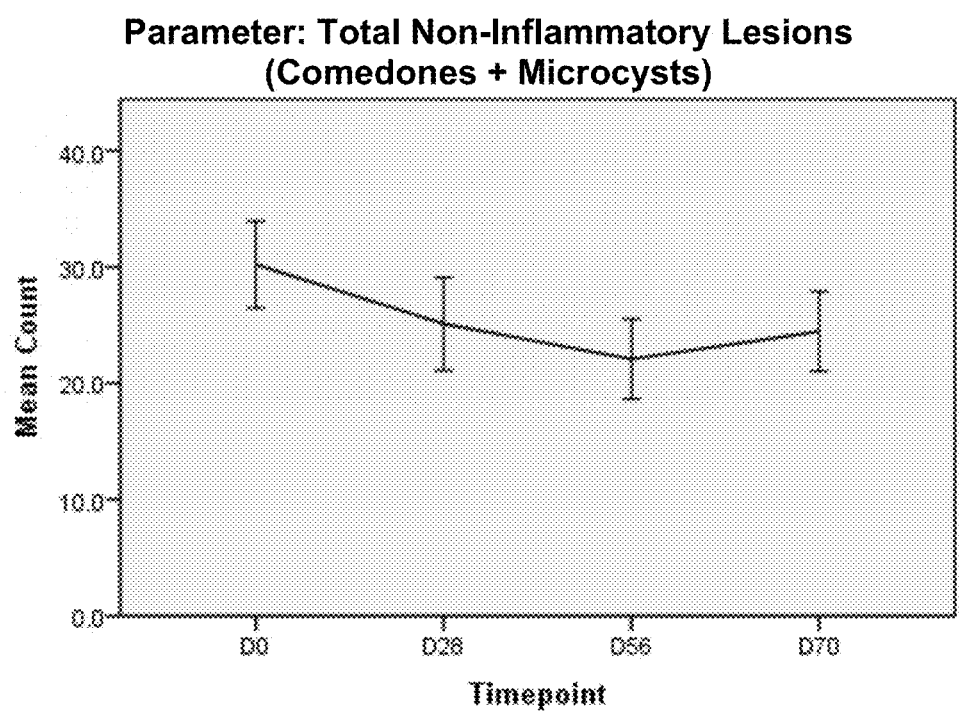
FIG. 7. Shows the evolution of the mean count of total non-inflammatory lesions across time of volunteers under daily use of an anhydrous sunscreen composition according to the present invention.

The anhydrous sunscreen compositions of the present invention can comprise, consist of, or consist essentially of the essential elements and limitations of the present invention described herein, as well as any of the additional or optional ingredients, components, or limitations described herein.

The terms "a", "an", and "the" are understood to encompass the plural as well as the singular.

As used herein, the expression "at least one" means one or more and thus includes individual components as well as mixtures/combinations.

All ranges and values disclosed herein are inclusive and combinable. For examples, any value or point described herein that falls within a range described herein can serve as a minimum or maximum value to derive a sub-range, etc.

The term "anhydrous" as used herein means that the sunscreen composition of the present invention, and the essential or optional components thereof, are substantially free of added or free water. From a formulation standpoint, this means that the sunscreen composition of the present invention contains less than about 5%, preferably less than about 3%, more preferably less than about 2% by weight, even more preferably less than about 1% by weight of free or added water.

In an embodiment, the anhydrous sunscreen composition of the present invention comprises:
(a) at least about 2% by weight of silica aerogel, relative to the total weight of the composition;
(b) at least one emollient selected from the group consisting of diisopropyl sebacate, diisopropyl adipate, carbonates, isopropyl myristate, dicaprilyl eter, isononyl isononate or isododecane;
(c) UV filter system; and
(d) a wax blend comprising paraffin, microcrystalline wax, synthetic wax and at least one wax selected from the group consisting of *Oryza sativa* (rice) bran wax or polyethylene wax.

The composition according to the invention presents enhanced anti-oiliness and anti-acne properties, high SPF values, good hardness, dry touch to the skin after application combined with matt effect and no white film formation.

In a preferred embodiment, the amount of silica aerogel in the anhydrous sunscreen composition of the present invention is from about 2% by weight to about 10% by weight, more preferably from about 2% by weight to about 8% by weight, relative to the total weight of the composition.

The silica aerogel is preferably hydrophobic silica aerogel, more preferably silica silylate.

The amount of the at least one emollient in the anhydrous sunscreen composition of the present invention is preferably at least about 10% by weight, relative to the total weight of the composition, more preferably from about 10% by weight to about 40% by weight, even more preferably from about 10% by weight to about 30% by weight, relative to the total weight of the composition.

Preferably, the sunscreen composition of the present invention is free of butters and high viscosity emollients, such as high viscosity silicons or *Ricinus communis* (castor) seed oil, *Theobroma cacao* (cocoa) seed butter, or butyrospermum parkii (shea) butter, thereby avoiding oily sensation and greasy effect on the skin after the application.

In a preferred embodiment, the anhydrous sunscreen composition of the present invention has an amount of UV filter system ranging from about 0.1% by weight to about 50% by weight, preferably from about 1% by weight to about 40% by weight, more preferably from about 1% by weight to about 30% by weight, in relation to the total weight of the composition.

The UV filter system of the present invention may comprise at least one UV filter selected from the group of inorganic UV filters and organic UV filters, and mixtures thereof. In a preferred embodiment, the UV filter system comprise butyl methoxydibenzoylmethane, ethylhexyl salicylate, ethylhexyl triazone, octocrylene, drometrizole trisiloxane, bis-ethylhexyloxyphenol methoxyphenyl triazine, or mixtures thereof.

In a preferred embodiment, the amount of wax blend in the anhydrous sunscreen composition of the present invention is from about 5% by weight to about 40% by weight, more preferably from about 10% by weight to about 40% by weight, even more preferably from about 10% by weight to about 30% by weight, relative to the total weight of the composition.

In a preferred embodiment, the anhydrous sunscreen composition of the present invention comprises additional fatty compounds selected from the group of oils, waxes, fatty acids, fatty alcohols, and mixtures thereof. Said additional fatty compounds are preferably in an amount ranging from 10% by weight to 80% by weight, relative to the total weight of composition, preferably from about 20% by weight to about 80% by weight, more preferably from about 20% by weight to about 70% by weight, relative to the total weight of the composition. In a preferred embodiment, the additional fatty compounds are selected from the group of isohexadecane, cetyl alcohol, $C_{12}$-$C_{15}$ alkyl benzoate, isopropyl palmitate, soybean oil, and mixtures thereof.

In an alternative embodiment, the anhydrous sunscreen composition of the present invention comprises pigments in an amount ranging from about 0.1% to about 30% by weight, more preferably from about 1% to about 30% by weight, and most preferably from about 5% to about 25% by weight, relative to the total weight of the composition.

In another preferred embodiment, the composition of the present invention presents a SPF of at least 30, preferably 30, 50, 60, 70, 80, 90 or 100.

The anhydrous sunscreen composition of the invention can be used as a daily product for the skin and may be in the form of lotions, milks, creams, gels, gel creams, foams, sprays and sticks. In a preferred embodiment, the anhydrous sunscreen composition of the present invention is in the form of a stick.

In another preferred embodiment, the present invention is related to the use of a composition for manufacturing a product for preventing sunburn, which can be used as sunscreen daily product.

In an embodiment, the composition of the present invention is in the form of a stick having a hardness of 120 g to 200 g, measured by means of a Stable Micro Systems™ Needle probe, following a penetrometry protocol.

The present invention is also related to a process of manufacturing an anhydrous sunscreen composition that provides for the consumer the properties described above. The process according to the present invention comprise the steps of:

(a) melting and mixing the wax blend, the emollient and the UV filter system at a temperature ranging from 60 to 100° C.;
(b) optionally, incorporating the additional ingredients and the mixture of step (a) at a temperature ranging from 60 to 100° C.;
(c) incorporating the silica aerogel at a temperature ranging from 60 to 100° C.

Preferably, steps (a),(b) and (c) are carried out at a temperature ranging from about 70° C. to about 90° C., more preferably from about 80° C. to 90° C.

In a preferred embodiment, the additional fatty compounds are melted and mixed in step (a).

Silica Aerogel

The "silica aerogel" according to the present invention is a porous material obtained by replacing (by drying) the liquid component of a silica gel with air. Silica aerogels are generally synthesized via a sol-gel process in a liquid medium and then dried, usually by extraction with a supercritical fluid, such as, but not limited to, supercritical carbon dioxide ($CO_2$). This type of drying makes it possible to avoid shrinkage of the pores and of the material. The sol-gel process and the various drying processes are described in detail in Brinker, C. J., and Scherer, G. W., Sol-Gel Science: New York: Academic Press, 1990.

In a preferred embodiment, the amount of silica aerogel in the anhydrous sunscreen composition of the present invention is at least about 2% by weight, relative to the total weight of the composition, preferably from about 2% by weight to about 10% by weight, more preferably from about 2% by weight to about 8% by weight, relative to the total weight of the composition.

The hydrophobic silica aerogel particles used in the present invention have a specific surface area per unit of mass (SM) ranging from about 500 to about 1500 $m^2/g$, or alternatively from about 600 to about 1200 $m^2/g$, or alternatively from about 600 to about 800 $m^2/g$, and a size expressed as the mean volume diameter (D[0.5]), ranging from about 1 to about 30 μm, or alternatively from about 5 to about 25 μm, or alternatively from about 5 to about 20 μm, or alternatively from about 5 to about 15 μm. The specific surface area per unit of mass may be determined via the BET (Brunauer-Emmett-Teller) nitrogen absorption method described in the *Journal of the American Chemical Society*, vol. 60, page 309, February 1938, corresponding to the international standard ISO 5794/1. The BET specific surface area corresponds to the total specific surface area of the particles under consideration.

The size of the silica aerogel particles may be measured by static light scattering using a commercial granulometer such as the MasterSizer 2000 machine from Malvern. The data are processed on the basis of the Mie scattering theory. This theory, which is exact for isotropic particles, makes it possible to determine, in the case of non-spherical particles, an "effective" particle diameter. This theory is especially described in the publication by Van de Hulst, H. C., "Light Scattering by Small Particles," Chapters 9 and 10, Wiley, New York, 1957.

The silica aerogel particles used in the present invention may advantageously have a tamped (or tapped) density ranging from about 0.04 $g/cm^3$ to about 0.10 $g/cm^3$, or alternatively from about 0.05 $g/cm^3$ to about 0.08 $g/cm^3$. In the context of the present invention, this density, known as the tamped density, may be assessed according to the following protocol: 40 g of powder are poured into a measuring cylinder; the measuring cylinder is then placed on a Stay 2003 machine from Stampf Volumeter; the measuring cylinder is then subjected to a series of 2500 packing motions (this operation is repeated until the difference in volume between two consecutive tests is less than 2%); the final volume Vf of packed powder is then measured directly on the measuring cylinder. The tamped density is determined by the ratio m/Vf, in this instance 40/Vf (Vf being expressed in $cm^3$ and m in g).

According to one embodiment, the hydrophobic silica aerogel particles used in the present invention have a specific surface area per unit of volume Sv ranging from about 5 to about 60 $m^2/cm^3$, or alternatively from about 10 to about $S_V$ $m^2/cm^3$, or alternatively from about 15 to about 40 $m^2/cm^3$. The specific surface area per unit of volume is given by the relationship: $S_V = S_M \cdot r$ where r is the tamped density expressed in $g/cm^3$ and SM is the specific surface area per unit of mass expressed in $m^2/g$, as defined above.

In some embodiments, the silica aerogel particles, according to the invention, have an oil-absorbing capacity, measured at the wet point, ranging from about 5 to about 18 ml/g, or alternatively from about 6 to about 15 ml/g, or alternatively from about 8 to about 12 ml/g. The oil-absorbing capacity measured at the wet point, noted Wp, corresponds to the amount of water that needs to be added to 100 g of particle in order to obtain a homogeneous paste. Wp is measured according to the wet point method or the method for determining the oil uptake of a powder described in standard NF T 30-022. Wp corresponds to the amount of oil adsorbed onto the available surface of the powder and/or absorbed by the powder by measuring the wet point, described below: An amount =2 g of powder is placed on a glass plate, and the oil (isononyl isononanoate) is then added dropwise. After addition of 4 to 5 drops of oil to the powder, mixing is performed using a spatula, and addition of oil is continued until a conglomerate of oil and powder has formed. At this point, the oil is added one drop at a time and the mixture is then triturated with the spatula. The addition of oil is stopped when a firm, smooth paste is obtained. This paste must be able to be spread on the glass plate without cracking or forming lumps. The volume Vs (expressed in ml) of oil used is then noted. The oil uptake corresponds to the ratio Vs/m.

The aerogels used, according to the present invention, are hydrophobic silica aerogels, preferably of silylated silica (INCI name: silica silylate). The term "hydrophobic silica" means any silica whose surface is treated with silylating agents, for example, halogenated silanes, such as alkylchlorosilanes, siloxanes, in particular dimethylsiloxanes, such as hexamethyldisiloxane, or silazanes, so as to functionalize the OH groups with silyl groups Si—Rn, for example, trimethylsilyl groups. Preparation of hydrophobic silica aerogel particles that have been surface-modified by silylation, is found in U.S. Pat. No. 7,470,725, incorporated herein by reference. In one embodiment, hydrophobic silica aerogel particles surface-modified with trimethylsilyl groups are desirable.

Suitable examples of hydrophobic silica aerogels, may include, but are not limited to, the aerogels sold under the tradenames of VM-2260 (INCI name: Silica silylate) and VM-2270 (INCI name: Silica silylate), both available from Dow Corning Corporation (Midland, Michigan). The particles of VM-2260 have a mean size of about 1000 microns and a specific surface area per unit of mass ranging from 600 to 800 $m^2/g$. The particles of VM-2270 have a mean size ranging from 5 to 15 microns and a specific surface area per unit of mass ranging from 600 to 800 $m^2/g$. Another suitable example of a hydrophobic silica aerogel may include, but is not limited to, the aerogels commercially available from Cabot Corporation (Billerica, Massachusetts) under the tradename of Aerogel TLD 201, Aerogel OGD 201 and Aerogel TLD 203, Enova Aerogel MT 1100 and Enova Aerogel MT 1200.

The silica aerogel is preferably hydrophobic silica aerogel, more preferably silica silylate.

UV Filters System

The composition, according to the present invention, comprises a UV filter system. The UV filter system may comprise at least one UV filter selected from the group of inorganic UV filters and organic UV filters, and mixtures thereof.

The composition, according to the present invention, may comprise the UV filter system in an amount of from about 0.1% by weight to about 50% by weight, and in some embodiments from about 1% by weight to about 40% by weight, and in some embodiments from about 1% by weight to about 30% by weight in relation to the total weight of the composition.

Inorganic UV Filters

The composition, according to the present invention, comprise a UV filter system comprising at least one inorganic UV filter. If two or more inorganic UV filters are used, they may be the same or different.

The inorganic UV filter used for the present invention may be active in the UV-A and/or UV-B region. The inorganic UV filter may be hydrophilic and/or lipophilic. The inorganic UV filter is in some embodiments insoluble in solvents, such as water, and ethanol commonly used in cosmetics.

It is in some embodiments desirable that the inorganic UV filter be in the form of a fine particle such that the mean (primary) particle diameter thereof ranges from about 1 nm to about 50 nm, and in some embodiments from about 5 nm to about 40 nm, and in some embodiments from about 10 nm to about 30 nm. The mean (primary) particle size or mean (primary) particle diameter here is an arithmetic mean diameter.

The inorganic UV filter can be selected from the group consisting of silicon carbide, metal oxides which may or may not be coated, and mixtures thereof. And in some embodiments, the inorganic UV filters are selected from pigments (mean size of the primary particles: generally from about 5 nm to about 50 nm, and in some embodiments from about 10 nm to about 50 nm) formed of metal oxides, such as, for example, pigments formed of titanium oxide (amorphous or crystalline in the rutile and/or anatase form), iron oxide, zinc oxide, zirconium oxide, or cerium oxide, which are all UV photoprotective agents that are well known per se. And in some embodiments, the inorganic UV filters are selected from titanium oxide, zinc oxide, and, in some embodiments, titanium oxide.

The inorganic UV filter may or may not be coated. The inorganic UV filter may have at least one coating. The coating may comprise at least one compound selected from the group consisting of alumina, silica, aluminum hydroxide, silicones, silanes, fatty acids or salts thereof (such as sodium, potassium, zinc, iron, or aluminum salts), fatty alcohols, lecithin, amino acids, polysaccharides, proteins, alkanolamines, waxes, such as beeswax, (meth)acrylic polymers, organic UV filters, and (per)fluoro compounds. It is in some embodiments desirable for the coating to include at least one organic UV filter. As the organic UV filter in the coating, a dibenzoylmethane derivative, such as butyl methoxydibenzoylmethane (Avobenzone) and 2,2'-Methylenebis[6-(2H-Benzotriazol-2-yl)-4-(I,I,3,3-Tetramethyl-Butyl) Phenol] (Methylene Bis-Benzotriazolyl Tetramethylbutylphenol), such as marketed as "TINOSORB M" by BASF, may be desirable.

In a known manner, the silicones in the coating(s) may be organosilicon polymers or oligomers comprising a linear or cyclic and branched or cross-linked structure, of variable molecular weight, obtained by polymerization and/or polycondensation of suitable functional silanes and essentially composed of repeated main units in which the silicon atoms are connected to one another via oxygen atoms (siloxane bond), optionally substituted hydrocarbon radicals being connected directly to said silicon atoms via a carbon atom.

The term "silicones" also encompasses silanes necessary for their preparation, in particular alkylsilanes.

The silicones used for the coating(s) can be and in some embodiments are selected from the group consisting of alkylsilanes, polydialkylsiloxanes, and polyalkylhydrosiloxanes. And in some embodiments still, the silicones are selected from the group consisting of octyltrimethylsilane, polydimethylsiloxanes, and polymethylhydrosiloxanes.

Of course, the inorganic UV filters made of metal oxides may, before their treatment with silicones, have been treated with other surfacing agents, in particular with cerium oxide, alumina, silica, aluminum compounds, silicon compounds, or their mixtures. The coated inorganic UV filter may have been prepared by subjecting the inorganic UV filter to one or more surface treatments of a chemical, electronic, mechano-chemical, and/or mechanical nature with any of the compounds as described above, as well as polyethylenes waxes, metal alkoxides (titanium or aluminum alkoxides), metal oxides, sodium hexametaphosphate, and those shown, for example, in Cosmetics & Toiletries, February 1990, Vol. 105, pp. 53-64.

The coated inorganic UV filters may be titanium oxides coated: with silica, such as the product "Sun veil" from Ikeda, and "Sunsil TIN 50" from Sunjin Chemical; with silica and with iron oxide, such as the product "Sunveil F" from Ikeda; with silica and with alumina, such as the products "Microtitanium Dioxide MT 500 SA" from Tayca, "Tioveil" from Tioxide, and "Mirasun TiW 60" from Rhodia; with alumina, such as the products "Tipaque TTO-55 (B)" and "Tipaque TTO-55 (A)" from Ishihara, and "UVT 14/4" from Kemira; with alumina and with aluminum stearate, such as the product "Microtitanium Dioxide MT 100 T, MT 100 TX, MT 100 Z or MT-01" from Tayca, the products "Solaveil CT-10 W" and "Solaveil CT 100" from Uniqema, and the product "Eusolex T-AVO" from Merck; with alumina and with aluminum laurate, such as the product "Microtitanium Dioxide MT 100 S" from Tayca; with iron oxide and with iron stearate, such as the product "Microtitanium Dioxide MT 100 F" from Tayca; with zinc oxide and with zinc stearate, such as the product "BR351" from Tayca; with silica and with alumina and treated with a silicone, such as the products "Microtitanium Dioxide MT 600 SAS", "Microtitanium Dioxide MT 500 SAS", and "Microtitanium Dioxide MT 100 SAS" from Tayca; with silica, with alumina and with aluminum stearate and treated with a silicone, such as the product "STT-30-DS" from Titan Kogyo; with silica and treated with a silicone, such as the product "UV-Titan X 195" from Kemira; with alumina and treated with a silicone, such as the products "Tipaque TTO-55 (S)" from Ishihara or "UV Titan M 262" from Kemira; with triethanolamine, such as the product "STT-65-S" from Titan Kogyo; with stearic acid, such as the product "Tipaque TTO-55 (C)" from Ishihara; or with sodium hexametaphosphate, such as the product "Microtitanium Dioxide MT 150 W" from Tayca. Other titanium oxide pigments treated with a silicone are, and in some embodiments $TiO_2$ treated with octyltrimethylsilane and for which the mean size of the individual particles is from 25 and 40 nm, such as that marketed under the trademark "T 805" by Degussa Silices, $TiO_2$ treated with a polydimethylsiloxane and for which the mean size of the individual particles is 21 nm, such as that marketed under the trademark "70250 Cardre UF $TiO_2Si_3$" by Cardre, and anatase/rutile $TiO_2$ treated with a polydimethylhydrosiloxane and for which the mean size of the individual particles is 25 nm, such as that marketed under the trademark "Microtitanium Dioxide USP Grade Hydrophobic" by Color Techniques.

And in some embodiments, the following coated $TiO_2$ can be used as the coated inorganic UV filter: Stearic acid (and) Aluminum Hydroxide (and) $TiO_2$, such as the product "MT-100 TV" from Tayca, with a mean primary particle diameter of 15 nm; Dimethicone (and) Stearic Acid (and) Aluminum Hydroxide (and) $TiO_2$, such as the product "SA-TTO-S4" from Miyoshi Kasei, with a mean primary particle diameter of 15 nm; Silica (and) $TiO_2$, such as the product "MT-100 WP" from Tayca, with a mean primary particle diameter of 15 nm; Dimethicone (and) Silica (and) Aluminum Hydroxide (and) $TiO_2$, such as the product "MT-Y02" and "MT-Y-110 M3S" from Tayca, with a mean primary particle diameter of 10 nm; Dimethicone (and) Aluminum Hydroxide (and) $TiO_2$, such as the product "SA-TTO-S3" from Miyoshi Kasei, with a mean primary particle diameter of 15 nm; Dimethicone (and) Alumina (and) $TiO_2$, such as the product "UV TITAN MI 70" from Sachtleben, with a mean primary particle diameter of 15 nm;. and Silica (and) Aluminum Hydroxide (and) Alginic Acid (and) $TiO_2$, such as the product "MT-100 AQ" from Tayca, with a mean primary particle diameter of 15 nm. In terms of UV filtering ability, $TiO_2$ coated with at least one organic UV filter is more desirable. For example, Avobenzone (and) Stearic Acid (and) Aluminum Hydroxide (and) $TiO_2$, such as the product "HXMT-100ZA" from Tayca, with a mean primary particle diameter of 15 nm, can be used.

The uncoated titanium oxide pigments are, for example, marketed by Tayca under the trademarks "Microtitanium Dioxide MT500B" or "Microtitanium Dioxide MT600B", by Degussa under the trademark "P 25", by Wacker under the trademark "Oxyde de titane transparent PW", by Miyoshi Kasei under the trademark "UFTR", by Tomen under the trademark "ITS" and by Tioxide under the trademark "Tioveil AQ". The uncoated zinc oxide pigments are, for example, those marketed under the trademark "Z-cote" by Sunsmart; those marketed under the trademark "Nanox" by Elementis; and those marketed under the trademark "Nanogard WCD 2025" by Nanophase Technologies. The coated zinc oxide pigments are, for example, those marketed under the trademark "Oxide Zinc CS-5" by Toshiba (ZnO coated with polymethylhydrosiloxane); those marketed under the trademark "Nanogard Zinc Oxide FN" by Nanophase Technologies (as a 40% dispersion in Finsolv TN, $C_{12}$-$C_{15}$ alkyl benzoate); those marketed under the trademark "Daitopersion Zn-30" and "Daitopersion Zn-50" by Daito (dispersions in oxyethylenated polydimethylsiloxane/cyclopolymethylsiloxane comprising 30% or 50% of zinc nano-oxides coated with silica and polymethylhydrosiloxane); those marketed under the trademark "NFD Ultrafine ZnO" by Daikin (ZnO coated with phosphate of perfluoroalkyl and a copolymer based on perfluoroalkylethyl as a dispersion in cyclopentasiloxane); those marketed under the trademark "SPD-Z1" by Shin-Etsu (ZnO coated with a silicone-grafted acrylic polymer dispersed in cyclodimethylsiloxane); those marketed under the trademark "Escalol Z100" by ISP (alumina-treated ZnO dispersed in an ethylhexyl methoxycinnamate/PVP-hexadecene copolymer/methicone mixture); those marketed under the trademark "Fuji ZnO-SMS-10" by Fuji Pigment (ZnO coated with silica and polymethylsilsesquioxane); and those marketed under the trademark "Nanox Gel TN" by Elementis (ZnO dispersed at 55% in $C_{12}$-$C_{15}$ alkyl benzoate with hydroxystearic acid polycondensate). The uncoated cerium oxide pigments are marketed, for example, under the trademark "Colloidal Cerium Oxide" by Rhone-Poulenc.

The uncoated iron oxide pigments are, for example, marketed by Arnaud under the trademarks "Nanogard WCD 2002 (FE 45B)", "Nanogard Iron FE 45 BL AQ", "Nanogard FE 45R AQ", and "Nanogard WCD 2006 (FE 45R)", or by Mitsubishi under the trademark "TY-220".

The coated iron oxide pigments are, for example, marketed by Arnaud under the trademarks "Nanogard WCD 2008 (FE 45B FN)", "Nanogard WCD 2009 (FE 45B 556)", "Nanogard FE 45 BL 345", and "Nanogard FE 45 BL", or by BASF under the trademark "Oxyde de fer transparent".

Mention may also be made of mixtures of metal oxides, in particular, of titanium dioxide and of cerium dioxide, including a mixture of equal weights of titanium dioxide coated with silica and of cerium dioxide coated with silica, such as marketed by Ikeda under the trademark "Sunveil A", and also a mixture of titanium dioxide and of zinc dioxide coated with alumina, with silica and with silicone, such as the product "M 261" marketed by Kemira, or coated with alumina, with silica and with glycerol, such as the product "M 211" marketed by Kemira.

Coated inorganic UV filters are desirable, because the UV filtering effects of the inorganic UV filters can be enhanced. In addition, the coating(s) may help uniformly or homogeneously disperse the UV filters in the composition, according to the present invention.

Organic UV Filters

The composition, according to the present invention, comprises a UV filter system comprising at least one organic UV filter. If two or more organic UV filters are used, they may be the same or different.

The organic UV filter used for the present invention may be active in the UV-A and/or UV-B region. The organic UV filter may be hydrophilic and/or lipophilic.

The organic UV filter may be solid or liquid. The terms "solid" and "liquid" mean solid and liquid, respectively, at 25° C. under 1 atm.

The organic UV filter can be selected from the group consisting of anthranilic compounds; dibenzoylmethane compounds; cinnamic compounds; salicylic compounds; camphor compounds; benzophenone compounds; 8,8-diphenylacrylate compounds; triazine compounds; benzotriazole compounds; benzalmalonate compounds; benzimidazole compounds; imidazoline compounds; bis-benzoazolyl compounds; p-aminobenzoic acid (PABA) compounds; methylenebis(hydroxyphenylbenzotriazole) compounds; benzoxazole compounds; screening polymers and screening silicones; dimers derived from a-alkylstyrene; 4,4-diarylbutadienes compounds; guaiazulene and derivatives thereof; rutin and derivatives thereof; flavonoids; bioflavonoids; oryzanol and derivatives thereof; quinic acid and derivatives thereof; phenols; retinol; cysteine; aromatic amino acids; peptides having an aromatic amino acid residue; and mixtures thereof.

Mention may be made, as examples of the organic UV filter(s), of those denoted below under their INCI names, and mixtures thereof. Anthranilic compounds: menthyl anthranilates, such as marketed under the trademark "Neo Heliopan MA" by Haarmann and Reimer. The dibenzoylmethane compounds: Butyl methoxydibenzoylmethane, such as marketed in particular under the trademark "Parsol 1789" by Hoffmann-La Roche; and isopropyl dibenzoylmethane. Cinnamic compounds: Ethylhexyl methoxycinnamate, such as marketed in particular under the trademark "Parsol MCX" by Hoffmann-La Roche; isopropyl methoxycinnamate; isopropoxy methoxycinnamate; isoamyl methoxycinnamate, such as marketed under the trademark "Neo Heliopan E 1000" by Haarmann and Reimer; cinoxate (2-ethoxyethyl-4-methoxy cinnamate); DEA methoxycinnamate; diisopropyl methylcinnamate; and glyceryl ethylhexanoate dimethoxycinnamate. Salicylic compounds: Homosalate (homomentyl salicylate), such as marketed under the trademark "Eusolex HMS" by Rona/EM Industries; ethylhexyl salicylate, such as marketed under the trademark "Neo Heliopan OS" by Haarmann and Reimer; glycol salicylate; butyloctyl salicylate; phenyl salicylate; dipropyleneglycol salicylate, such as marketed under the trademark "Dipsal" by Scher; and TEA salicylate, such as marketed under the trademark "Neo Heliopan TS" by Haarmann and Reimer. Camphor compounds, in particular, benzylidenecamphor derivatives: 3-benzylidene camphor, such as manufactured under the trademark "Mexoryl SD" by Chimex; 4-methylbenzylidene camphor, such as marketed under the trademark "Eusolex 6300" by Merck; benzylidene camphor sulfonic acid, such as manufactured under the trademark "Mexoryl SL" by Chimex; camphor benzalkonium methosulfate, such as manufactured under the trademark "Mexoryl SO" by Chimex; terephthalylidene dicamphor sulfonic acid, such as manufactured under the trademark "Mexoryl SX" by Chimex; and polyacrylamidomethyl benzylidene camphor, such as manufactured under the trademark "Mexoryl SW" by Chimex. Benzophenone compounds: Benzophenone-1 (2,4-dihydroxybenzophenone), such as marketed under the trademark "Uvinul 400" by BASF; benzophenone-2 (Tetrahydroxybenzophenone), such as marketed under the trademark "Uvinul D50" by BASF; Benzophenone-3 (2-hydroxy-4-methoxybenzophenone) or oxybenzone, such as marketed under the trademark "Uvinul M40" by BASF; benzophenone-4 (hydroxymethoxy benzophonene sulfonic acid), such as marketed under the trademark "Uvinul MS40" by BASF; benzophenone-5 (Sodium hydroxymethoxy benzophenone Sulfonate); benzophenone-6 (dihydroxy dimethoxy benzophenone); such as marketed under the trademark "Helisorb 11" by Norquay; benzophenone-8, such as marketed under the trademark "Spectra-Sorb UV-24" by American Cyanamid; benzophenone-9 (Disodium dihydroxy dimethoxy benzophenonedisulfonate), such as marketed under the trademark "Uvinul DS-49" by BASF; and benzophenone-12, and n-hexyl 2-(4-diethylamino-2-hydroxybenzoyl)benzoate (such as UVINUL A+by BASF). 8,8-Diphenylacrylate compounds: Octocrylene, such as marketed in particular under the trademark "Uvinul N539" by BASF; and Etocrylene, such as marketed in particular under the trademark "Uvinul N35" by BASF. Triazine compounds: Diethylhexyl butamido triazone, such as marketed under the trademark "Uvasorb HEB" by Sigma 3V; 2,4,6-tris(dineopentyl 4'-aminobenzalmalonate)-s-triazine, bis-ethylhexyloxyphenol methoxyphenyl triazine, such as marketed under the trademark «TINOSORB S» by CIBA GEIGY, and ethylhexyl triazone, such as marketed under the trademark «UVTNUL T150» by BASF. Benzotriazole compounds, in particular, phenylbenzotriazole derivatives: 2-(2H-benzotriazole-2-yl)-6-dodecyl-4-methylpheno, branched and linear; and those described in U.S. Pat. No. 5,240,975. Benzalmalonate compounds: Dineopentyl 4'-methoxybenzalmalonate, and polyorganosiloxane comprising benzalmalonate functional groups, such as polysilicone-15, such as marketed under the trademark "Parsol SLX" by Hoffmann-LaRoche. Benzimidazole compounds, in particular, phenylbenzimidazole derivatives: Phenylbenzimidazole sulfonic acid, such as marketed in particular under the trademark "Eusolex 232" by Merck, and disodium phenyl dibenzimidazole tetrasulfonate, such as marketed under the trademark "Neo Heliopan AP" by Haarmann and Reimer. Imidazoline compounds: Ethylhexyl dimethoxybenzylidene dioxoimidazoline propionate. Bis-benzoazolyl compounds: The derivatives as described in EP-669,323 and U.S. Pat. No. 2,463, 264. Para-aminobenzoic acid compounds: PABA (p-aminobenzoic acid), ethyl PABA, Ethyl dihydroxypropyl PABA, pentyl dimethyl PABA, ethylhexyl dimethyl PABA, such as marketed in particular under the trademark "Escalol 507" by ISP, glyceryl PABA, and PEG-25 PABA, such as marketed under the trademark "Uvinul P25" by BASF. Methylene bis-(hydroxyphenylbenzotriazol) compounds, such as 2,2'-methylenebis[6-(2H-benzotriazol-2-yl)-4-methyl-phenol], such as marketed in the solid form under the trademark "Mixxim BB/200" by Fairmount Chemical, 2,2'-methylenebis[6-(2H-benzotriazol-2-yl)-4-(1,1,3,3-tetramethylbutyl)phenol], such as marketed in the micronized form in aqueous dispersion under the trademark "Tinosorb M" by BASF, or under the trademark "Mixxim BB/100" by Fairmount Chemical, and the derivatives as described in U.S. Pat. Nos. 5,237,071 and 5,166,355, GB-2,303,549, DE-197, 26,184, and EP-893,119, and Drometrizole trisiloxane, such as marketed under the trademark "Silatrizole" by Rhodia Chimie or-"Mexoryl XL" by L'Oréal. Benzoxazole compounds: 2,4-bis[5-I(dimethylpropyl)benzoxazol-2-yl-(4-phenyl)imino]-6-(2-ethylhexyl)imino-1,3,5-triazine, such as marketed under the trademark of Uvasorb K2A by Sigma 3V. Screening polymers and screening silicones: The silicones described in WO 93/04665. Dimers derived from a-alkylstyrene: The dimers described in DE-19855649. 4,4-Diarylbutadiene compounds:1,1-dicarboxy(2,2'-dimethylpropyl)-4,4-diphenylbutadiene.

It is in some embodiments desirable that the organic UV filter(s) be selected from the group consisting of: butyl methoxydibenzoylmethane, ethylhexyl methoxycinnamate, homosalate, ethylhexyl salicylate, octocrylene, phenylbenzimidazole sulfonic acid, benzophenone-3, benzophenone-4, benzophenone-5, n-hexyl 2-(4-diethylamino-2-hydroxybenzoyl)benzoate, 1,r-(1,4-piperazinediyl)bis[1-[244-(diethylamino)-2-hydroxybenzoyl]phenyl]-methanone 4-methylbenzylidene camphor, terephthalylidene dicamphor sulfonic acid, disodium phenyl dibenzimidazole tetrasulfonate, ethylhexyl triazone, bis-ethylhexyloxyphenol methoxyphenyl triazine, diethylhexyl butamido triazone, 2,4,6-tris(dineopentyl 4'-aminobenzalmalonate)-s-triazine, 2,4,6-tris(diisobutyl 4'-aminobenzalmalonate)-s-triazine, 2,4-bis-(n-butyl 4'-aminobenzalmalonate)-6-[(3-{1,3,3,3-tetramethyl-1-[(trimethylsilyloxy]-disiloxanyl}propyl) amino]-s-triazine, 2,4,6-tris-(di-phenyl)-triazine, 2,4,6-tris-(ter-phenyl)-triazine, methylene bis-benzotriazolyl tetramethylbutylphenol, drometrizole trisiloxane, polysilicone-15, dineopentyl 4'-methoxybenzalmalonate, 1,1-dicarboxy(2,2'-dimethylpropyl)-4,4-diphenylbutadiene, 2,4-bis

[5-I (dimethylpropyl)benzoxazol-2-yl-(4-phenyl)imino]-6-(2-ethylhexyl)imino-1,3,5-triazine, camphor benzylkonium methosulfate, and mixtures thereof.

Emollient

The anhydrous sunscreen composition according to the present invention comprises at least one emollient selected from the group consisting of diisopropyl sebacate, diisopropyl adipate, carbonates, isopropyl myristate, dicaprilyl eter, isononyl isononate or isododecane.

In a preferred embodiment, the amount of the at least one emollient in the anhydrous sunscreen composition of the present invention is preferably at least about 10% by weight, relative to the total weight of the composition, more preferably from about 10% by weight to about 40% by weight, even more preferably from about 10% by weight to about 30% by weight, relative to the total weight of the composition.

The anhydrous composition according of the present invention is preferably free of high-viscosity emollient, such as high viscosity silicons or *Ricinus communis* (castor) seed oil, *Theobroma cacao* (cocoa) seed butter, or butyrospermum parkii (shea) butter, thereby avoiding oily sensation and greasy effect on the skin after the application.

Wax Blend

The anhydrous sunscreen composition according to the present invention comprises a specific wax blend comprising paraffin, microcrystalline wax, synthetic wax and at least one wax selected from the group consisting of *Oryza sativa* (rice) bran wax or polyethylene wax. In a preferred embodiment, the at least one wax is polyethylene.

In a preferred embodiment, the amount of wax blend in the anhydrous sunscreen composition of the present invention is from about 5% by weight to about 40% by weight, more preferably from about 10% by weight to about 40% by weight, even more preferably from about 10% by weight to about 30% by weight, relative to the total weight of the composition.

Preferably, the amount of the at least one wax in the anhydrous sunscreen composition of the present invention is from about 4% by weight to about 30% by weight, more preferably from about 8% by weight to about 30% by weight, even more preferably from about 8% by weight to about 25% by weight, relative to the total weight of the composition.

Additional Fatty Compounds

In addition to the constituents of the anhydrous sunscreen composition described above, the composition of the present invention can also comprise additional fatty compounds selected from oils, waxes, fatty acids, fatty alcohols, and mixtures thereof. As used herein, the term "additional fatty compounds" does not include the wax blend described above.

The proportion of additional fatty compounds in the anhydrous sunscreen composition according to the invention is generally from about 10% by weight to about 80% by weight, relative to the total weight of composition, preferably from about 20% by weight to about 80% by weight, more preferably from about 20% by weight to about 70% by weight, relative to the total weight of the composition.

The waxes useful for the present invention may be of mineral, fossil, animal, or vegetable origin, hydrogenated oils, or mixtures thereof. Non-limiting examples of waxes include hydrocarbon-based waxes such as beeswax, ouricury wax, Japan wax, cork fiber waxes or sugar cane waxes, euphorbia cerifera (candelilla) wax, copernicia cerifera (carnauba) wax, lignite waxes, lanolin wax, montan wax, ozokerites, ethylenediamine/stearyl dimer dilinoleate copolymer, hydrogenated oils and glycerides that are solid at 25° C. It is also possible to use silicone waxes, among which mention may be made of alkyl, alkoxy and/or esters of polymethylsiloxane.

Oils which can be used in the invention, mention may be made to polar or slightly polar oils, i.e. oils including an alkyl chain, preferably a $C_3$-$C_{40}$ alkyl chain. Non-limiting examples of oils to be used in the present invention include:

linear or branched hydrocarbons such as liquid paraffin, isohexadecane, liquid petroleum jelly and light naphthalene oils, and lanolin, hydrocarbon-based oils of plant origin, such as glyceride triesters, which are generally triesters of fatty acids and of glycerol, the fatty acids of which can have varied chain lengths from $C_4$ to $C_{24}$, it being possible for these chains to be saturated or unsaturated and linear or branched; these oils are in particular wheat germ oil, sunflower oil, grape seed oil, sesame oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin seed oil, marrow oil, blackcurrant oil, evening primrose oil, millet oil, barley oil, quinoa oil, rye oil, safflower oil, candlenut oil, passionflower oil and musk rose oil; or also caprylic/capric acid triglycerides, synthetic esters, for instance oils of formula RCOOR' in which R represents a linear or branched fatty acid residue containing from 1 to 40 carbon atoms and R' represents a hydrocarbon-based chain that is especially branched, containing from 1 to 40 carbon atoms, on condition that R+R' is ≥10, for instance, cetearyl octanoate, isopropyl palmitate, $C_{12}$-$C_{15}$ alkyl benzoate, 2-ethylphenyl benzoate, isopropyl lanolate, hexyl laurate, isononyl isononanoate, oleyl erucate, 2-ethylhexyl palmitate, isostearyl isostearate, octanoates, decanoates or ricinoleates of alcohols or polyalcohols, such as propylene glycol dioctanoate; hydroxylated esters, such as isostearyl lactate or diisostearyl malate; and pentaerythritol esters; citrates or tartrates, such as di(linear $C_{12}$-$C_{13}$ alkyl) tartrates, and also di(linear $C_{14}$-$C_{15}$ alkyl) tartrates, or acetates.

silicone oils such as polydimethylsiloxanes (PDMS's), optionally including a $C_3$-$C_{40}$ alkyl or alkoxy chain or a phenyl chain, such as phenyltrimethicones, optionally fluorinated polyalkylmethylsiloxanes, such as polymethyltrifluoropropyldimethylsiloxanes, or with functional groups such as hydroxyl, thiol and/or amine groups; polysiloxanes modified with fatty acids, fatty alcohols or polyoxyalkylenes, fluorosilicones and perfluoro oils;

mixtures thereof.

Non-liming examples of fatty alcohols useful for the present invention are those liquid at room temperature, containing a branched and/or unsaturated carbon-based chain containing from 12 to 26 carbon atoms, for instance octyldodecanol, isostearyl alcohol, behenyl alcohol, oleyl alcohol, 2-hexyldecanol, 2-butyloctanol or 2-undecylpentadecanol.

Non-limiting examples of fatty acids useful for the present invention are higher fatty $C_{12}$-$C_{22}$ acids, such as oleic acid, linoleic acid or linolenic acid.

Pigments

In an alternative embodiment, the anhydrous sunscreen composition according to the present invention may comprise pigments. The suitable pigments used in the anhydrous sunscreen composition of the present invention may be coated or uncoated.

The coated pigments are pigments which have undergone one or more surface treatments of a chemical, electronic, mechanochemical and/or mechanical nature with compounds such as those described for example in Cosmetics & Toiletries, February 1990, vol. 105, p.53-64, such as amino acids, beeswax, fatty acids, fatty alcohols, anionic surface-active agents, lecithin, sodium, potassium, zinc, iron or aluminum salts of fatty acids, (titanium or aluminum) metal alkoxides, polyethylene wax, silicones, proteins (collagen, elastin), alkanolamines, silicon oxides, metal oxides or sodium hexametaphosphate.

Coated pigments are more particularly titanium oxides coated with silica, silica and iron oxide, silica and alumina, alumina and aluminum stearate, alumina and aluminum laurate, iron oxide and iron stearate, zinc oxide and zinc stearate, silica, alumina and silicone, alumina, aluminum stearate and silicone, alumina and silicone, etc.

Mixtures of metal oxides may also be mentioned, especially titanium dioxide and cerium dioxide, including the silica-coated equiponderous mixture of titanium dioxide and cerium dioxide, as well as the alumina-silica- and silicone-coated mixture of titanium oxide and zinc dioxide, or the alumina-, silica- and glycerin-coated mixture of titanium dioxide and zinc dioxide.

In addition, uncoated iron oxides, titanium oxides, zinc oxides and cerium oxide may be used in the sunscreen composition of the present invention.

The amount of the pigments in the anhydrous sunscreen composition of the invention preferably ranges from about 0.1% to about 30% by weight, more preferably from about 1% to about 30% by weight, and most preferably from about 5% to about 25% by weight, relative to the total weight of the composition.

Additional Ingredients

In addition to the essential components described hereinbefore, the composition of the invention may further comprise any usual cosmetically acceptable ingredient, which may be chosen especially from perfume/fragrance, preserving agents, antioxidants, solvents, actives, vitamins, fillers, silicones, polymers, and mixtures thereof.

A person skilled in the art will take care to select the optional additional ingredients and/or the amount thereof such that the advantageous properties of the composition according to the invention are not, or are not substantially, adversely affected by the envisaged addition.

Suitable polymers include, but are not limited to, aluminum starch octenylsuccinate, xanthan gum, poly $C_{10-30}$ alkyl acrylate, acrylates/$C_{10-30}$ alkyl acrylate crosspolymer, styrene/acrylates copolymer, and mixtures thereof.

Non-limiting example of preserving agent which can be used in accordance with the invention include phenoxyethanol. An example of antioxidant is pentaerythrityl tetra-di-t-butyl hydroxyhydrocinnamate.

Suitable fillers of the invention could be as examples of oil-absorbing fillers: mica, silica, zea may (corn) starch, magnesium oxide, nylon-12, nylon-66, cellulose, talc, talc (and) methicone, talc (and) dimethicone, perlite, sodium silicate, pumice, PTFE, polymethyl methacrylate, *Oryza sativa* (rice) starch, aluminum starch octenylsuccinate, potato starch modified, alumina, calcium sodium borosilicate, magnesium carbonate, dimethicone/vinyl dimethicone crosspolymer, sodium carboxylmethyl starch.

Suitable solvents include, but are not limited alcohols, glycols and polyols such as glycerin, caprylyl glycol, pentylene glycol, propylene glycol, butylene glycol, and mixtures thereof.

Suitable additional actives include, but are not limited to, disodium EDTA, triethanolamine, and mixtures thereof.

Non-limiting example of vitamins suitable for the composition of the present invention includes tocopherol.

Exemplary of polymers, include, but not limited to, aluminum starch octenylsuccinate, xanthan gam, acrylates/$C_{10-30}$ alkyl acrylate crosspolymer and styrene/acrylates copolymer.

The additional ingredients may represent from 0.1% to 20%, such as from 0.1% to 10% or such as from 0.1 to 8% by weight of the total weight of the composition of the invention.

By way of non-limiting illustration, the invention will now be described with reference to the following examples.

EXAMPLES

Examples 1 TO 7

Anhydrous sunscreen compositions according to the present invention were prepared according to examples 1, 2 and 7 below. Comparative anhydrous sunscreen compositions were prepared according to examples 3 to 6.

| FUNCTION | INGREDIENT | EX. 1 | EX. 2 | EX. 3 | EX. 4 | EX. 5 | EX. 6 | EX. 7 |
|---|---|---|---|---|---|---|---|---|
| PIGMENTS | IRON OXIDES | 0 | 0 | 3 | 0.5 | 1 | 0.8 | 0.5 |
| | IRON OXIDES | 0 | 0 | 1.5 | 6 | 1 | 3 | 2.2 |
| | IRON OXIDES | 0 | 0 | 1 | 3 | 5 | 0.5 | 1.1 |
| | TITANIUM DIOXIDE | 0 | 0 | 4 | 1 | 7 | 6 | 12 |
| UV FILTER | BIS-ETHYLHEXYLOXYPHENOL METHOXYPHENYL TRIAZINE | 1 | 8 | 2 | 2 | 2 | 0.5 | 1 |
| | BUTYL METHOXYDIBENZOYLMETHANE | 7 | 5 | 8 | 4 | 4 | 3 | 4 |
| | ETHYLHEXYL SALICYLATE | 2 | 5 | 2 | 5 | 5 | 1 | 5 |
| | ETHYLHEXYL TRIAZONE | 4 | 3 | 5 | 3.5 | 1.5 | 3.5 | 1 |
| | OCTOCRYLENE | 1 | 3.5 | 3 | 3.5 | 3.5 | 0.4 | 3.5 |
| | DROMETRIZOLE TRISILOXANE | 1 | 2 | 2 | 4 | 2 | 1 | 2 |

-continued

| FUNCTION | INGREDIENT | EX. 1 | EX. 2 | EX. 3 | EX. 4 | EX. 5 | EX. 6 | EX. 7 |
|---|---|---|---|---|---|---|---|---|
| WAXES | MICROCRYSTALLINE WAX | 2.5 | 4 | 1.5 | 4 | 3 | 7 | 5 |
| | PARAFFIN | 3 | 2.1 | 6 | 6 | 3 | 4 | 2 |
| | SYNTHETIC WAX | 3 | 0.8 | 1.5 | 1 | 0.6 | 1.1 | 0.4 |
| | POLYETHYLENE WAX | 15 | 0 | 0 | 0 | 0 | 0 | 16 |
| | BEHENYL ALCOHOL | 0 | 0 | 0 | 14 | 0 | 0 | 0 |
| | *EUPHORBIA CERIFERA* (CANDELILLA) WAX | 0 | 0 | 0 | 0 | 14 | 0 | 0 |
| | *COPERNICIA CERIFERA* (CARNAUBA) WAX | 0 | 0 | 0 | 0 | 0 | 17 | 0 |
| | *ORYZA SATIVA* (RICE) BRAN WAX | 0 | 14 | 0 | 0 | 0 | 0 | 0 |
| | ETHYLENEDIAMINE/STEARYL DIMER DILINOLEATE COPOLYMER | 0 | 0 | 9 | 0 | 0 | 0 | 0 |
| ADDITIONAL FATTY COMPOUNDS | ISOPROPYL PALMITATE | 17.2 | 28 | 22.5 | 17.8 | 15 | 17 | 7.7 |
| | ISOHEXADECANE | 5 | 4.5 | 7 | 5 | 7 | 3 | 4 |
| | C12-15 ALKYL BENZOATE | 5 | 3 | 5 | 5 | 8 | 5 | 5 |
| | *GLYCINE SOJA* (SOYBEAN) OIL | 1 | 0.1 | 0.4 | 0.2 | 0.3 | 0.1 | 0.4 |
| EMOLLIENT | DIISOPROPYL SEBACATE | 29 | 12 | 14 | 10 | 13 | 19 | 23 |
| SILICA AEROGEL | SILICA SILYLATE | 2.5 | 4 | 2 | 2.5 | 4 | 7 | 3 |
| ADDITIONAL INGREDIENTS | FRAGRANCE | 0.5 | 0 | 0 | 0 | 0 | 0 | 0.5 |
| | TOCOPHEROL | 0.3 | 1 | 0.5 | 2 | 0.1 | 0.1 | 0.7 |
| | PENTAERYTHRITYL TETRA-DI-T-BUTYL HYDROXYHYDROCINNAMATE | 0 | 0 | 0.1 | 0 | 0 | 0 | 0 |

Example 7

The compositions according to Examples 1, 2 and 7 were prepared according to the following steps:
  (a) melting and mixing of the fatty compounds, the emollient and the UV filter system at a temperature ranging from 80° C. to 90° C.;
  (b) incorporating the additional ingredients to the mixture of step (a) at a temperature ranging from 80° C. to 90° C.
  (c) incorporating the silica aerogel at a temperature ranging from 80 to 90° C.

For the composition according to Example 7, the pigments were added in step (b).

Example 8

In order to compare the hardness of the sunscreen compositions according to the present invention, a hardness test was performed wherein the compositions according to examples 1 to 6 were subjected to a penetrometry protocol, measured by means of a Stable Micro Systems™ Needle probe.

The hardness results, shown in FIG. 1, demonstrate that anhydrous sunscreen compositions comprising polyethylene wax or *Oryza sativa* (rice) bran wax, according to examples 1 and 2, have enhanced hardness when compared with compositions according to examples 3 to 6.

Example 9

An anti-acne clinical study was started to evaluate the anti-acne and comedogenic potential of the anhydrous sunscreen composition according to Example 1 by counting lesions (papules, pustules, comedones and microcysts) dermatologists and self-assessment. The test was performed with 60 female volunteers from 18 to 40 years old having skin phototype II to IV according to Fitzpatrick scale.

The volunteers presented acne grade 1 or 2, with at least 5 inflammatory lesions (papules and pustules) and 10 comedones or microcysts at the inclusion visit and oily skin with tendency to face acne (70 mg/cm$^2$) evaluated using the Sebumeter equipment.

There were used four different time of assessment: D0 (baseline), D28 (28 days after of application), D56 (56 days after application) and D70 (14 days after stopping using the product). The mean count of papules, pustules, comedones and microcysts were evaluated.

FIGS. 2 to 7 show, respectively the mean count results of papules, pustules, total inflammatory lesions (sum of papules and pustules), comedones, microcysts and total noninflammatory lesions (sum of comedones and microcysts) of the group of volunteers.

It is possible that the use of the anhydrous sunscreen composition according to the present invention has proved to be capable of causing a significantly decrease in lesions number until D56 in normal use conditions. The maintenance of the face skin condition 14 days after interruption of the investigational product was maintained only in relation to the pustules and microcysts.

Example 10

The face oiliness of the volunteers was evaluated using Sebumeter SM 815 to determine the level of sebum, wherein the mean values of three linear areas of the central region of the forehead were evaluated.

Subsequently the measurement of the sebaceous excretion rate was made after 30 min of the participant's forehead skin delipidation with 2 ml of 70% ethanol.

There were used four different time of assessment: D0 (baseline), D28 (28 days after of application), D56 (56 days after application) and D70 (14 days after stopping using the product).

Figure 8:
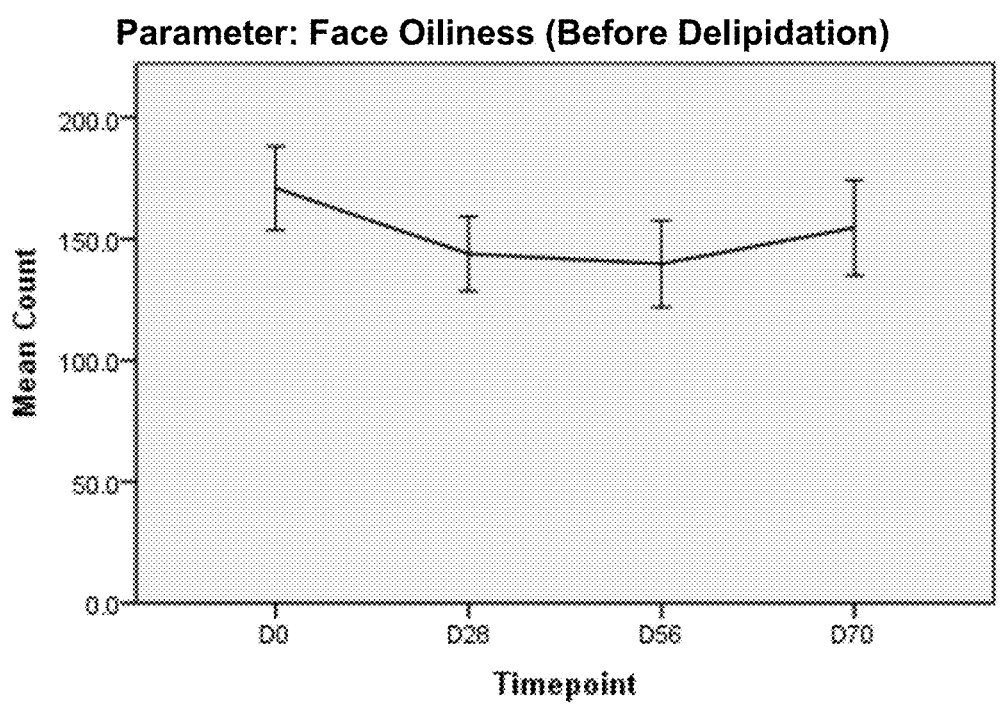
FIG. 8. Shows the evolution of the mean count of face oiliness (before delipidation) across time of volunteers under daily use of an anhydrous sunscreen composition according to the present invention.
Figure 9:
FIG. 9. Shows the evolution of the mean count of sebaceous excretion rate (after delipidation) across time of volunteers under daily use of an anhydrous sunscreen composition according to the present invention.

FIGS. 8 and 9 show the results for face oiliness and sebaceous excretion rate for a continuous use of a composition according to Example 1. It is possible to observe that the subject's face skin oiliness significantly reduced using the anhydrous sunscreen composition according to the present invention before and after delipidation.

The invention claimed is:
1. An anhydrous sunscreen composition, comprising:
 (a) at least 2% by weight of silica aerogel, relative to the total weight of the composition;
 (b) at least one emollient selected from the group consisting of diisopropyl sebacate, diisopropyl adipate, carbonates, isopropyl myristate, dicaprilyl ether, isononyl isononate and isododecane; and
 (c) a UV filter system; and
 (d) a wax blend comprising paraffin, microcrystalline wax, synthetic wax and at least one wax selected from the group consisting of Oryza sativa (rice) bran wax and polyethylene wax.

2. The anhydrous sunscreen composition, according to claim 1, wherein the amount of silica aerogel in the sunscreen composition is from 2% by weight to 10% by weight, relative to the total weight of the composition.

3. The anhydrous sunscreen composition, according to claim 1, wherein the amount of the at least one emollient in the sunscreen composition is from 10% by weight to 40% by weight, relative to the total weight of the composition.

4. The anhydrous sunscreen composition, according to claim 1, wherein the amount of the UV filter system in the sunscreen composition is from 0.1% by weight to 50% by weight, relative to the total weight of the composition.

5. The anhydrous sunscreen composition, according to claim 1, wherein the amount of wax blend in the sunscreen composition is from 5% by weight to 40% by weight, relative to the total weight of the composition.

6. The anhydrous sunscreen composition, according to claim 1, wherein the silica aerogel is a hydrophobic silica aerogel.

7. The anhydrous sunscreen composition, according to claim 1, wherein the UV filter system comprises at least one UV filter selected from the group consisting of inorganic UV filters and organic UV filters.

8. The anhydrous sunscreen composition, according to claim 7, wherein the UV filter system comprises at least one organic UV filter selected from the group consisting of anthranilic compounds; dibenzoylmethane compounds; cinnamic compounds; salicylic compounds; camphor compounds; benzophenone compounds; β,β-diphenylacrylate compounds; triazine compounds; benzotriazole compounds; benzalmalonate compounds; benzimidazole compounds; imidazoline compounds; bis-benzoazolyl compounds; p-aminobenzoic acid (PABA) compounds; methylenebis (hydroxyphenylbenzotriazole) compounds; benzoxazole compounds; screening polymers and screening silicones; dimers derived from a-alkylstyrene; 4,4-diarylbutadienes compounds; guaiazulene and derivatives thereof; rutin and derivatives thereof; flavonoids; bioflavonoids; oryzanol and derivatives thereof; quinic acid and derivatives thereof; phenols; retinol; cysteine; aromatic amino acids; peptides having an aromatic amino acid residue; and mixtures thereof.

9. The anhydrous sunscreen composition, according to claim 7, wherein the UV filter system comprises at least one inorganic UV filter selected from the group consisting of silicon carbide, coated or uncoated metal oxides, and mixtures thereof.

10. The anhydrous sunscreen composition, according to claim 1, further comprising additional fatty compounds in an amount ranging from 10% by weight to 80% by weight, relative to the total weight of composition.

11. The anhydrous sunscreen composition, according to claim 10, wherein the fatty compounds are selected from the group of oils, waxes, fatty acids, fatty alcohols, and mixtures thereof.

12. The anhydrous sunscreen composition, according to claim 1, further comprising pigments in an amount ranging from 0.1% to 30% by weight, relative to the total weight of the composition.

13. The anhydrous sunscreen composition, according to claim 1, wherein the composition is in the form of a stick.

14. A process of manufacturing an anhydrous sunscreen composition according to claim 1, comprising:
 (a) melting and mixing the wax blend, the emollient and the UV filter system at a temperature ranging from 60 to 100° C.;
 (b) optionally, incorporating additional ingredients to the mixture of step (a) at a temperature ranging from 60 to 100° C.
 (c) incorporating the silica aerogel at a temperature ranging from 60 to 100° C.

15. The process according to claim 14, further comprising melting and mixing the additional fatty compounds in step (a).

16. A method for protecting skin from UV light comprising applying the anhydrous sunscreen composition of claim 1 to the skin.

17. The method of claim 16, wherein the anhydrous sunscreen composition is in the form of a stick.

18. The anhydrous sunscreen composition, according to claim 1, wherein the amount of silica aerogel in the sunscreen composition is from 2% by weight to 10% by weight, relative to the total weight of the composition; the amount of the at least one emollient in the sunscreen composition is from 10% by weight to 40% by weight, relative to the total weight of the composition; the amount of the UV filter system in the sunscreen composition is from 0.1% by weight to 50% by weight, relative to the total weight of the composition, and the amount of wax blend in the sunscreen composition is from 5% by weight to 40% by weight, relative to the total weight of the composition.

19. The anhydrous sunscreen composition, according to claim 18, wherein the at least one wax is polyethylene wax.

* * * * *